United States Patent [19]

Farrell

[11] Patent Number: 4,692,413

[45] Date of Patent: Sep. 8, 1987

[54] USE OF RLDM ™ 1-6 AND OTHER LIGNINOLYTIC ENZYMES FOR THE DECOLORIZATION OF E1 EFFLUENT

[75] Inventor: Roberta L. Farrell, Danvers, Mass.

[73] Assignee: Repligen Corporation, Cambridge, Mass.

[21] Appl. No.: 845,657

[22] Filed: Mar. 28, 1986

Related U.S. Application Data

[63] Continuation-in-part of Ser. No. 755,245, Jul. 15, 1985, abandoned.

[51] Int. Cl.[4] .................... D21C 3/00; D21C 3/20; C12R 1/645; C02F 3/00
[52] U.S. Cl. .................................. 435/278; 162/72; 210/606; 435/911
[58] Field of Search ................. 162/72; 210/606, 611; 435/278

[56] References Cited

PUBLICATIONS

Alberti, B. N. and Klibanov, A. M., (1981), "Enzymatic Removal of Dissolved Aromatics from Industrial Aqueous Effluents", Biotechnology and Bioengineering Symp. 11:373-379.

Primary Examiner—Lionel M. Shapiro
Attorney, Agent, or Firm—Roman Saliwanchik; David R. Saliwanchik

[57] ABSTRACT

Disclosed is a novel process for decolorization of E1 effluent. Specifically, novel enzymes, designated rLDM ™, and other ligninolytic enzymes present in the extracellular growth medium from a fermentation of *Phanerochaete chrysosporium*, are used to decolorize the effluent.

18 Claims, No Drawings

USE OF RLDM TM 1-6 AND OTHER LIGNINOLYTIC ENZYMES FOR THE DECOLORIZATION OF E1 EFFLUENT

CROSS REFERENCE TO A RELATED APPLICATION

This is a continuation-in-part of my copending application Ser. No. 755,245, filed Jul. 15, 1985, now abandoned.

BACKGROUND OF THE INVENTION

The primary chemical method for making pulp from wood involves the digestion of lignin in the wood with sodium sulfide and sodium hydroxide. This is termed the sulfate or kraft process.

Wood pulp produced in the kraft process generally contains 5-8% by weight of residual, modified lignin which gives pulp a characteristic brown color. To obtain pulp of very high brightness and brightness stability, the lignin must be removed by certain oxidizing agents commonly referred to as bleaching chemicals. Many bleaching processes exist but almost all begin with the chlorination-extraction (C-E) stage. The spent liquor from the first alkali extraction stage of bleaching following chlorination, commonly referred to as E1 effluent, contains over 70% of the effluent color emanating from a kraft bleach plant (Alberti, B. N. and Klibanov, A. M. [1981] Biotech. and Bioeng. Symp. 11: 373-379). The effluent must be discharged due to its high content of corrosive chlorides. Polymeric lignin degradation products, the main contributors to color of bleach plant effluents, are resistant to the current bacteria-based effluent treatment process. Alternate treatment processes such as ultrafiltration, carbon adsorption, and massive lime precipitation are required for effective color removal, but are quite expensive. Economical color-removal systems do not presently exist and would be desirable for effluent treatment prior to its discharge to receiving waters.

Fungal decolorization systems have been studied. In USDA sponsored laboratory experiments (Kirk, T. K. [1983] in The Filamentous Fungi, Vol. 4, Fungal Technology, Smith, J. E., Berry, D. R., Kristiansen, B., eds., Edward Arnold Press, London), greater than 80% decolorization of bleaching effluent prepared by chlorination and alkali treatment of kraft-cooked synthetic lignins has been achieved in 24 hr using *Phanerochaete chrysosporium* cultures.

There are three problems in using fungal cultures to decolorize bleach plant effluents: (1) fungi require careful culture conditions (i.e., humidity, aeration, temperature and pH) not compatible with industrial processing environments; (2) fungi require long lag times and then only very slowly degrade lignin; and (3) fungi cannot grow on lignin. An additional food source must be added to support fungal growth.

BRIEF SUMMARY OF THE INVENTION

The subject invention concerns the decolorization of E1 effluent by treating the effluent with rLDM TM and other ligninolytic enzymes present in the extracellular growth medium from a fermentation of *Phanerochaete chrysosporium*. rLDM TM are ligninases which are highly specific and which will degrade lignin polymers. rLDM TM do not require precise culture conditions and are immediately active to efficiently decolorize effluents in a non-corrosive and non-polluting manner.

The lignin-degrading enzymes of the invention, referred to as rLDM TM, are referred to as Pulpases TM in co-pending application Ser. No. 755,245.

DETAILED DESCRIPTION OF THE INVENTION

The rLDM TM which can be used in the subject invention process were isolated from a novel stable mutant strain of the white-rot fungus *Phanerochaete chrysosporium*. The novel strain, designated SC26, has been deposited in the permanent collection of a public culture repository, to be maintained for at least 30 years. The culture repository is the Northern Regional Research Laboratory, U.S. Department of Agriculture, Peoria, Ill. 61604, USA. The accession number is NRRL 15978, and the deposit date is Jul. 3, 1985. This deposited culture is available to the public upon the grant of a patent disclosing it. The deposit also is available as required by foreign patent laws in countries wherein counterparts of the subject application, or its progeny, are filed. However, it should be understood that the availability of a deposit does not constitute a license to practice the subject invention in derogation of patent rights granted by governmental action.

Novel mutant SC26 was obtained by UV mutagenesis of the wild type *Phanerochaete chrysosporium*, ATCC 24725.

Novel mutant SC26 was grown on a nitrogen-limited trace element medium supplemented with glucose and buffered at pH 4.5.

Ligninase activity in the fermentation medium was measured periodically by standard means determining the rate of oxidation of veratryl alcohol to veratrylaldehyde.

Isolation and purification of the ligninases from the extracellular fluid in the fermentation was accomplished by ultrafiltration and fast protein liquid chromatography (FPLC) using an anion exchange column.

The rLDM TM used in the subject invention process were prepared as follows:

PREPARATIVE

EXAMPLE 1

Growth of Mutant SC26 (NRRL 15978) to Produce Fermentation Medium Containing Novel Ligninases Inoculum was prepared by homogenizing 50 ml of 1.5-day cultures of mutant SC26 grown in 1 liter flasks containing the following medium, designated nitrogen-limited BIII/glucose medium:

The BIII medium contains $1.08 \times 10^{-3}$ M ammonium tartrate, $1.47 \times 10^{-2}$ M $KH_2PO_4$, $2.03 \times 10^{-3}$ M $MgSO_4.7H_2O$, $6.8 \times 10^{-4}$ M $CaCl_2.2H_2O$, $2.96 \times 10^{-6}$ M thiamine.HCl and 10 ml.$L^{-1}$ of a trace element solution. The trace element solution contains $7.8 \times 10^{-3}$ M nitriloacetic acid, $1.2 \times 10^{-2}$ M $MgSO_4.7H_2O$, $1.7 \times 10^{-2}$ M NaCl, $3.59 \times 10^{-4}$ M $FeSO_4.7H_2O$, $7.75 \times 10^{-4}$ M $CoCl_2$, $9.0 \times 10^{-4}$ M $CaCl_2$, $3.48 \times 10^{-4}$ M $ZnSO_4.7H_2O$, $4 \times 10^{-5}$ M $CuSO_4.5H_2O$, $2.1 \times 10^{-5}$ M $AlK(SO_4)_2.12H_2O$, $1.6 \times 10^{-4}$ M $H_3BO_3$, $4.1 \times 10^{-5}$ M $NaMoO_4.2H_2O$ and $2.9 \times 10^{-3}$ M $MnSO_4.H_2O$.

The medium was supplemented with 10% (by wt/liter) of glucose.

The medium was buffered with 10 mM trans-aconitic acid, pH 4.5.

Flasks (125 ml, containing 10 ml sterile medium having the above-described medium) were each inoculated with 0.5 ml of the above homogenate and kept stationary at 39° C. The flasks were flushed on days 0, 3, and 6 with water-saturated $O_2$. Alternatively, a rotating biological contractor (RBC) was used to grow the fungus. 2.5 liters of the above-described medium was inoculated with 100 ml of the above homogenate and grown at 39° C. with the RBC rotating at 1 rpm with continuous oxygenation.

Ligninase activity was measured periodically by determining the rate of oxidation of veratryl alcohol to veratrylaldehyde. Reaction mixtures contained 275 μl of extracellular fluid (from flasks or the RBC), 2 mM veratryl alcohol, 0.4 mM $H_2O_2$ and 0.1 mM sodium tartrate, pH 2.5 in a final volume of 0.5 ml. The reactions were started by $H_2O_2$ addition immediately after buffer was added and were monitored at 310 nm. Protein was determined according to Bradford (Bradford, M. M. [1976] Anal. Biochem. 72:248–254) using bovine serum albumin (Sigma Chemical, St. Louis, MO) as standard.

PREPARATIVE EXAMPLE 2

Isolation and Purification of the Novel rLDM TM

The extracellular growth media from cultures grown in flasks, as described above, was harvested by centrifugation at 5000×G, 10 min, 4° C. Extracellular growth media was then concentrated by ultrafiltration through a 10K filter. The resulting concentrate is called the Ligninolytic Mixture TM. The rLDM TM contained in this Ligninolytic Mixture TM were separated by fast protein liquid chromatography (FPLC) using a Pharmacia Mono Q column (Pharmacia, Piscataway, N.J.) and a gradient of sodium acetate buffer, pH 6, from 10 mM to 1 M. rLDM TM 1, 2, 3, 4, 5, and 6 elute from the column in a typical preparation at the following sodium acetate molarities, respectively: 0.16, 0.18, 0.34, 0.40, 0.58, and 0.43 M to give essentially pure rLDM TM 1–6. Each rLDM TM is substantially free of other rLDM TM and native proteins.

Characterization of the Novel rLDM TM

The rLDM TM have been characterized by the following criteria:
(1) ability to catalyze the oxidation of veratryl alcohol to veratrylaldehyde;
(2) molecular weight as determined by SDS-PAGE;
(3) amino acid composition;
(4) heme content;
(5) homology by antibody reactivity;
(6) specificity of activity against lignin model substrates; and
(7) elution from an FPLC column at specified sodium acetate molarities.

All of the rLDM TM catalyze the oxidation of veratryl alcohol to veratrylaldehyde, as monitored spectrophotometrically at 310 nm. A unit of activity is defined as the production of 1 micromole of veratrylaldehyde in the rLDM TM catalyzed reaction. The specific activities of typical preparations at about 24° C. are as follows:

| rLDM TM | 1 | 2 | 3 | 4 | 5 | 6 |
|---|---|---|---|---|---|---|
| SPECIFIC ACTIVITY UNITS/MG · MINUTE | 2.6 | 17.1 | 5.1 | 9.7 | 9.4 | 12.4 |
| MOLECULAR WEIGHT kD | 38 | 38 | 42 | 42 | 43 | 42 |

Amino acid composition--See Table 1.

TABLE 1

Amino Acid Composition of rLDM TM

| Amino Acid | rLDM TM 1 Ratio | rLDM TM 2 Ratio | rLDM TM 3 Ratio | rLDM TM 5 Ratio | rLDM TM 6 Ratio |
|---|---|---|---|---|---|
| asp/asn | 1.4 | 2.0 | 5.4 | 5.0 | 3.0 |
| glu/gln | 6.0 | 7.7 | 16.8 | 19.9 | 8.0 |
| ser | 4.3 | 4.1 | 14.0 | 22.3 | 6.8 |
| his | 4.4 | 3.2 | 7.3 | 15.9 | 3.2 |
| gly | 6.5 | 5.7 | 24.0 | 44.7 | 8.3 |
| thr | 2.2 | 3.5 | — | — | 4.9 |
| arg | 1.1 | 1.2 | 2.9 | 4.8 | 1.3 |
| ala | 7.3 | 7.9 | 14.4 | 13.8 | 6.7 |
| tyr | 0.2 | — | 1.0 | 1.0 | 0.2 |
| met | — | — | 1.2 | — | 0.14 |
| val | 1.6 | 2.6 | 7.4 | 6.5 | 4.2 |
| phe | 1.1 | 3.0 | 7.0 | 3.3 | 3.2 |
| ile | 1.0 | 2.2 | 4.1 | 3.6 | 2.4 |
| leu | 1.5 | 2.6 | 6.5 | 6.0 | 3.3 |
| lys | 0.5 | 1.0 | 2.5 | 2.3 | 1.0 |

Heme and carbohydrate content—rLDM TM 1, 2, 3, 4, 5, and 6 each contain a single protoheme IX moiety. All are glycosylated according to periodic acid staining (PAS) and binding to Con A-Sepharose (Sigma).

Immunoblot Procedure

This procedure was used to further characterize the rLDM TM. It is a standard procedure which is disclosed in Towbin et al. (Towbin, H., Staehelin, T. and Gordon, J. [1979] Proc. Natl. Acad. Sci. USA 76: 4350). The procedure involves separating the proteins by electrophoresis in a gel, transfer of the proteins to a solid matrix, and reacting with (1) a primary probe, rabbit ant-rLDM TM antibody and (2) a secondary probe, goat anti-rabbit antibody coupled to horseradish peroxidase.

rLDM TM 1, 3, 4, 5, and 6 react to polyclonal antibodies made to rLDM TM 2 and 6, using the above immunoblot procedure. rLDM TM 2, in the same procedure, reacts to polyclonal antibodies made to rLDM TM 6.

All the rLDM TM disclosed herein have the following unique activities against lignin model substrates:
(1) oxidative cleavage of $C_\alpha$–$C_{62}$;
(2) hydroxylation of benzylic methylene groups;
(3) oxidation of benzyl alcohols to aldehydes;
(4) phenol oxidation; and
(5) oxidation of methoxy and ethoxy benzene.

"Lignin model substrates" are chemicals which resemble parts of lignin. The above activities are characteristic of the rLDM ™ disclosed herein.

Following are Examples which illustrate the best mode for practicing the invention. These Examples should not be construed as limiting. In all Examples herein, percentages are by weight and solvent mixture proportions are by volume unless otherwise noted.

EXAMPLE 1

Decolorization of Effluent with rLDM ™ and Other Ligninolytic Enzymes

The Ligninolytic Mixture ™, as described in Preparative Example 2, was added to a 0.2% solution of E1 effluent in 10 mM trans-aconitic acid, pH 4.5, 400 µM $H_2O_2$ and 100 µM $MnSO_4$. The solution was flushed with 2 and incubated with slow shaking at 39° C. for 12 hr. The solution was monitored spectrophotometrically in the ultraviolet and visible regions. E1 effluent treated as above was noticeably decolorized and reduced in absorbance at 465 nm. (Note that color is measured by A465 nm wherein an absorbance of 1.0 at 465 nm, pH 7.6 equals 3774 National Council for Air and Stream Improvement color units.)

The $MnSO_4$ is optional.

Regarding the above conditions, for each of the parameters there is a range of values which can be used to achieve the desired result. Typical values and acceptable ranges for each parameter are shown in Table 2.

EXAMPLE 2 rLDM ™ 1 through 6, individually, or mixtures thereof, can be used to treat effluent using essentially the same procedures as disclosed in Example 1, including ranges, or obvious modifications thereof. The resulting effluent is decolorized.

EXAMPLE 3

Upon substituting extracellular growth medium from a *Phanerochaete chrysosporium* fermentation, obtained as disclosed in Preparative Example 1, for the Ligninolytic Mixture ™ of Example 1, there is obtained decolorized Eeffluent.

EXAMPLE 4

Upon substituting the Ligninolytic Mixture ™ of Example 1 with a mixture comprising all of the following or any combination thereof: rLDM ™ 1-6, individually or mixtures thereof; Ligninolytic Mixture ™; and extracellular growth medium; there is obtained decolorized E1 effluent.

The rLDM ™ of the subject invention can be used in the crude form, in a purified form, wherein each rLDM ™ is substantially free of other rLDM ™ and native proteins, and in mixtures thereof. It is well within the skill of a person skilled in the art to adjust amounts of rLDM ™ used in accordance with the purity of the rLDM ™ preparation.

"Native proteins" as used herein refers to other proteins present in the extracellular fermentation medium, as described above.

TABLE 2

| Parameter | Typical | Range |
| --- | --- | --- |
| Concentration of effluent | 0.2% | 0.01 to 20% |
| Concentration of trans-aconitic acid* | 10 mM | 0.005 to 0.5 M |
| Concentration of Ligninolytic Mixture ™ | 1 VAO/Unit/ml** | 0.01 to 30 Units/ml |
| pH | 4.5 | 2 to 7 |
| Concentration of $H_2O_2$ | 400 µM | 2 µM to 10 mM |
| Concentration of $MnSO_4$ | 100 µM | 10 to 500 µM |
| Incubation period | 12 hr | 2 min to 48 hr |
| Temperature during incubation | 39° C. | 15° to 50° C. |

*Other nontoxic enzyme buffers such as ammonium tartrate can be used.
**VAO/Unit = veratryl alcohol oxidation activity unit

I claim:

1. A process for decolorizing E1 effluent which comprises treating said effluent with the Ligninolytic Mixture ™ from a *Phanerochaete chrysosporium* fermentation consisting essentially of rLDM ™ 1 through 6, and other ligninolytic enzymes.

2. A process, according to claim 1, wherein said *Phanerochaete chrysosporium* is the novel mutant strain designated SC26, having the identifying characteristics of NRRL 15978.

3. A process for decolorizing E1 effluent which comprises treating said effluent with enzymes consisting essentially of rLDM ™ 1 through 6, individually or with mixtures thereof.

4. A process, according to claim 1, wherein said Ligninolytic Mixture ™ from a fermentation of *Phanerochaete chrysosporium* is added to a solution of about 0.01 to about 20% E1 effluent, the effluent being in about 2 µM to about 10 mM of $H_2O_2$, and buffered at about pH 2 to about pH 7: the solution is then incubated with shaking at about 15° C. to about 50° C. for about 2 min to about 48 hr to obtain decolorized effluent.

5. A process, according to claim 1, wherein said Ligninolytic Mixture ™ from a fermentation of *Phanerochaete chrysosporium* is added to a solution of about 0.2% E1 effluent; the effluent is in about 400 µM of $H_2O_2$ and is buffered at about pH 4.5; the solution is then incubated with shaking at about 39° C. for about 12 hr to obtain decolorized effluent.

6. A process, according to claim 1, wherein about 10 to about 500 µM $MnSO_4$ is added with the Ligninolytic Mixture ™.

7. A process, according to claim 2, wherein about 10 to about 500 µM $MnSO_4$ is added with the Ligninolytic Mixture ™.

8. A process, according to claim 6, wherein the concentration of $MnSO_4$ is about 100 µM.

9. A process, according to claim 7, wherein the concentration of $MnSO_4$ is about 100 µM.

10. A process, according to claim 4, wherein said *Phanerochaete chrysosporium* is the novel mutant strain designated SC26, having the identifying characteristics of NRRL 15978.

11. A process, according to claim 5, wherein said *Phanerochaete chrysosporium* is the novel mutant strain designated SC26, having the identifying characteristics of NRRL 15978.

12. A process for decolorizing E1 effluent which comprises treating said effluent with the extracellular growth medium from a *Phanerochaete chrysosporium* fermentation consisting essentially of rLDM ™ 1 through 6, and other ligninolytic enzymes.

13. A process, according to claim 12, wherein said *Phanerochaete chrysosporium* is the novel mutant strain designated SC26, having the identifying characteristics of NRRL 15978.

14. A process, according to claim 12, wherein said extracellular growth medium from a fermentation of *Phanerochaete chrysosporium* is added to a solution of about 0.01 to about 20% E1 effluent, the effluent being in about 2 $\mu$M to about 10 mM of $H_2O_2$, and buffered at about pH 2 to about pH 7; the solution is then incubated with shaking at about 15° C. to about 50° C. for about 2 min to about 48 hr to obtain decolorized effluent.

15. A process, according to claim 12, wherein about 10 to about 500 $\mu$M $MnSO_4$ is added with the extracellular growth medium.

16. A process, according to claim 14, wherein said *Phanerochaete chrysosporium* is the novel mutant strain designated SC26, having the identifying characteristics of NRRL 15978.

17. A process for decolorizing E1 effluent which comprises treating said effluent with one or more of the following: rLDM TM 1 through 6, individually or a mixture thereof; Ligninolytic Mixture TM from a fermentation of *Phanerochaete chrysosporium* consisting essentially of rLDM TM 1 through 6, and other ligninolytic enzymes; and extracellular growth medium from a fermentation of *Phanerochaete chrysosporium* comprising rLDM TM 1 through 6, and other ligninolytic enzymes.

18. A process, according to claim 17, wherein said *Phanerochaete chrysosporium* is the novel mutant strain designated SC26, having the identifying characteristics of NRRL 15978.

* * * * *

UNITED STATES PATENT AND TRADEMARK OFFICE
CERTIFICATE OF CORRECTION

PATENT NO. : 4,692,413
DATED : September 8, 1987
INVENTOR(S) : Roberta L. Farrell It is certified that error appears in the above-identified patent and that said Letters Patent are hereby corrected as shown below:

Title: "RLDMTM" should read --rLDM$^{TM}$--.
Col. 1: line 2: "RLDMTM" should read --rLDM$^{TM}$--.
Col. 3: line 47: "5000XG" should read --5000 xG--; line 68: "composition:" should read --composition;--.
Col. 4: line 54: "ant-rLDM$^{TM}$" should read --anti-rLDM$^{TM}$--; line 64: "$C_\alpha$-$C_{62}$" should read --$C_\alpha$-$C_\beta$--.
Col. 5: line 18: "with $_2$" should read --with $O_2$--; line 44: "Eeffluent" should read --E1 effluent--.
Cla. 4: line 6: "pH 7:" should read --pH 7;--

Signed and Sealed this

Sixteenth Day of February, 1988

*Attest:*

DONALD J. QUIGG

*Attesting Officer*   *Commissioner of Patents and Trademarks*